United States Patent [19]
Huggenberger

[11] Patent Number: 5,496,293
[45] Date of Patent: Mar. 5, 1996

[54] ADVANCING MECHANISM FOR AN INJECTION DEVICE

[75] Inventor: Heinz Huggenberger, Grafenried, Switzerland

[73] Assignee: Medimpex Ets., Liechtenstein

[21] Appl. No.: 241,869

[22] Filed: May 12, 1994

[30] Foreign Application Priority Data

Apr. 6, 1993 [CH] Switzerland .................... 01685/93

[51] Int. Cl.⁶ .................................................. A61M 5/00
[52] U.S. Cl. ........................................... 604/208; 604/209
[58] Field of Search .................................. 604/207–210, 604/220, 232

[56] References Cited

U.S. PATENT DOCUMENTS

| | | | |
|---|---|---|---|
| 3,977,574 | 8/1976 | Thomas | 222/391 |
| 4,413,760 | 11/1983 | Paton | 222/309 |
| 4,456,450 | 6/1984 | Heling | 425/376 R |
| 4,710,172 | 12/1987 | Jacklich et al. | 604/118 |
| 4,883,472 | 11/1989 | Michel | 604/208 |
| 5,092,842 | 3/1992 | Bechtold et al. | 604/135 |
| 5,112,317 | 5/1992 | Michel | 604/208 |
| 5,244,465 | 9/1993 | Michel | 604/208 |
| 5,281,198 | 1/1994 | Haber et al. | 604/86 |
| 5,385,558 | 1/1995 | Cottone, Sr. et al. | 604/208 |

FOREIGN PATENT DOCUMENTS

| | | | |
|---|---|---|---|
| 0603401 | 10/1934 | Germany | 604/209 |
| 0622848 | 5/1949 | United Kingdom | 604/209 |
| 93024160 | 9/1993 | WIPO | 604/208 |

Primary Examiner—John D. Yasko
Assistant Examiner—Adam J. Cermak
Attorney, Agent, or Firm—Walter C. Farley

[57] ABSTRACT

A feed mechanism for an injection device having an ampoule casing (13) includes an outer casing (2), an inner casing (3) protruding rearwardly from the outer casing and a toothed rack (4) longitudinally displaceable with the inner casing against the force of a spring (8). The rack has teeth (5) of which the length L corresponds to one full injection dose. The inner casing is longitudinally movable by a length L between two stops (6, 7) in the inner and outer casings. The inner casing has a latch (9, 10) which detachably locks the inner casing at its extreme forward position into an aperture (11) of the ampoule casing. A pawl prevents return movement of the rack.

7 Claims, 1 Drawing Sheet

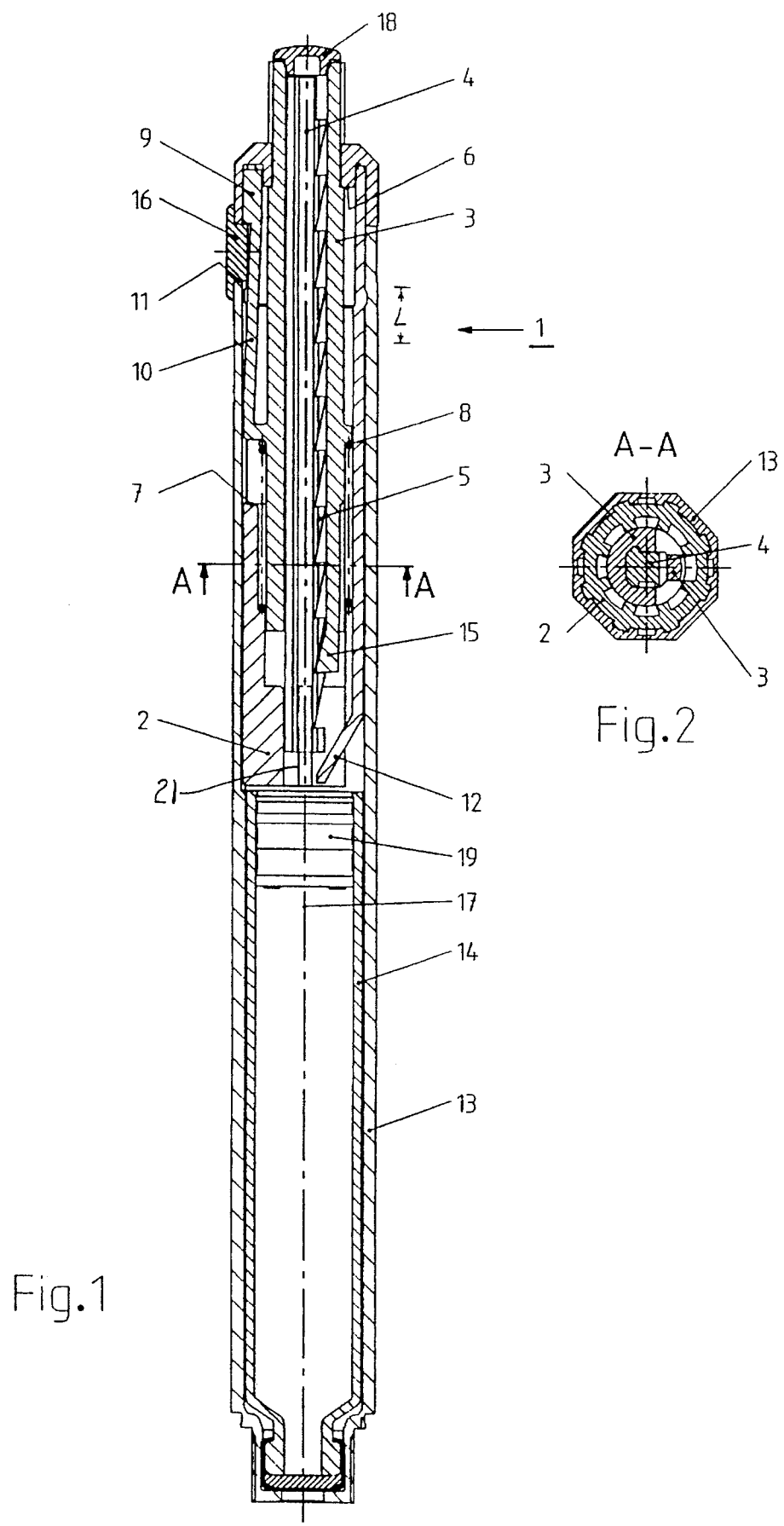

ADVANCING MECHANISM FOR AN INJECTION DEVICE

FIELD OF THE INVENTION

The invention relates to a feed mechanism for an injection device with an ampoule casing, an external casing and an inner casing rearwardly protruding from the outer one, and with a toothed rack displaceable by the inner casing against the force of a spring.

BACKGROUND OF THE INVENTION

A dosing system with a gear rack is known from European patent document B1 0,037,696. This system has the disadvantage that, by pressing the dosing button more than once, the patient may self-administer a medical overdose. Another disadvantage is that, as a rule, the proper dose is administered by moving forward several gear teeth, and that reciprocation of the dosing button in the longitudinal direction of a dosing stroke may result in overdosing.

SUMMARY OF THE INVENTION

An object of the invention is to provide a feed mechanism for an injection device which offers increased safety together with very simple operation.

The foregoing and other objects are achieved in accordance with the invention with a feed mechanism wherein (A) a gear rack has teeth of lengths L each corresponding to a full injection dose, (B) an inner casing is reciprocatingly movable by the length L between two stops in an outer casing, (C) the inner casing is fitted with snap-in means detachably stopping it when it reaches the extreme forward position, in an aperture of the ampoule casing, and (D) a recoil-safety means is provided for the gear rack.

The object is further achieved in accordance with the invention using an injection device with such a feed mechanism which is characterized by an ampoule casing receiving at its front part an ampoule and at its rear part the feed mechanism.

BRIEF DESCRIPTION OF THE DRAWINGS

A preferred embodiment of the invention is described below with reference to the following drawings wherein:

FIG. 1 is a longitudinal section of a device including a feed mechanism in accordance with the invention; and FIG. 2 is a transverse sectional view along line A—A of FIG. 1.

DETAILED DESCRIPTION OF THE PREFERRED EMBODIMENT

A device in accordance with the invention indicated generally at 1 in FIGS. 1 and 2 includes a feed mechanism insertable into an ampoule casing 13 to form an injection device. The feed mechanism includes an outer casing 2 and an inner casing 3 which is axially longitudinally movable within casing 2 and projects rearwardly out of outer casing 2. In this context, "front" refers to the end of the device from which medication is discharged and "rear" refers to the opposite end. A toothed rack 4 is within casing 3 and can be advanced by moving inner casing 3 against the force of a spring 8. Spring 8 is a compression coil spring acting against oppositely facing shoulders on casings 2 and 3 and urges the casings in opposite directions. At the outwardly protruding rear end of inner casing 3 is a dosing button 18.

Rack 4 has a preselected number of outwardly facing teeth 5 of uniform length, the length L of each tooth corresponding to one full injection dose. Inner casing 3 is longitudinally reciprocatingly movable by the length L between two shoulders defining stops 6 and 7 formed on outer casing 2.

Inner casing 3 has a snap-in safety device comprising a securing, radially outwardly spring-loaded spring arm 10 carrying a pawl 9. When the inner casing reaches its extreme forward position, pawl 9 snaps into a hole 11 formed through the wall of ampoule casing 13 because of the spring force of spring arm 10. The feed mechanism 1 is locked thereby and can be actuated again only after the pawl 9 has been disengaged from hole 11.

Inner casing 3 also has a pawl 15 at its front end engaging a tooth of gear rack 4, so that casing 3 presses the gear rack axially forward as casing 3 advances. A return preventing means is provided for the gear rack 4 and includes a pawl 12 fixed to outer casing 2 and extending inwardly at an angle toward longitudinal axis 17 of the feed system and entering the path of advance of the gear rack 4. As the rack is advanced, pawl 12 can engage a tooth of the rack forwardly of the tooth engaged by pawl 15.

Aperture 11 in ampoule casing 13 can be closed from the outside by inserting a removable safety button 16 which holds ratchet 9 of spring arm 10 in the rearmost position of the inner casing 3, whereby inner casing 3 is locked against axial movement relative to the outer casing 2.

The feed mechanism can be easily and simply slipped into ampoule casing 13 in which an ampoule 14 is received at its front portion, whereupon said feed mechanism forms a complete injection assembly in the form of an injection pen.

The operation of the feed mechanism 1 is as follows.

After removing the locking button 16 and placing a conventional needle (not shown) on the front end of ampoule casing 13, medicine carried in ampoule 14 can be dispensed by depressing dosing button 18. The axial length of the individual teeth 5 of gear rack 4 is selected so that one tooth 5 precisely corresponds to one dose. The user depresses the dosing button 18 until pawl 9 of safety spring arm 10 moves into aperture 11 of ampoule casing 13. A stem 21 at the end of rack 4 presses against an ampoule stopper 19, moving the stopper axially forward within the ampoule and discharging medicine from the ampoule. Dosing button 18 remains indexed in the forward position. Axial motion of dosing button 18 within the dosing height will not cause overdosing because the advance pawl 15 will remain within the same tooth during this process.

Simultaneously with the indexing of the ratchet 9 of the safety slider 10, return-preventing pawl 12 also indexes into a tooth 5. This ensures that when pawl 9 is removed from hole 11, thereby unlocking the dosing button, by depressing safety button 16, gear rack 4 is not dragged along when spring 8 causes dosing button 18 to slide back to its protruding position. Advance pawl 15 then snaps into a new tooth 5.

To prevent inadvertently displacing ampoule stopper 19 by the gear rack 4 and the dosing button 18 during shipping and storage, safety button 16 prevents axial displacement of the dosing button.

The medicine container, namely the ampoule 14 and the ampoule holder 13 (plastic pen) are provided as one functional unit to the user, that is, following discharge of the ampoule 14, the plastic pen no longer can be used.

What is claimed is:

1. A feed mechanism for an injection device comprising the combination of an outer casing (2);

an ampoule casing having an aperture;

a liquid-containing ampoule in said ampoule casing;

an inner casing (3) in said outer casing and protruding rearwardly from said outer casing (2), said inner casing being longitudinally movable relative to said outer casing in a forward direction manually, said inner and outer casings including stop means for limiting said relative movement to a distance (L);

spring means urging said inner casing in a rearward direction;

a toothed rack (4) having a plurality of teeth (5), each tooth having a length (L) corresponding to one full injection dose, said inner casing having means for engaging said rack and moving said rack forward longitudinally of said outer casing against the force of said spring means when said inner casing is moved manually, said rack being coupled to said ampoule to dispense liquid therefrom when said rack is moved forward;

latch means (9, 10) carried by said inner casing for releasably engaging said aperture (11) when said inner casing (3) reaches an extreme forward position to thereby prevent motion of said inner casing until said latch means is released; and recoil safety means (12) for preventing rearward motion of said rack.

2. A feed mechanism according to claim 1 wherein said latch means (9, 10) includes a spring, a slider arm carried by said inner casing and urged radially outwardly by said spring, and a pawl carried by said slider arm, said pawl (9) being positioned to enter said aperture when said extreme forward position is reached.

3. A feed mechanism according to claim 2 and including a removable safety button (16) for closing said aperture (11) from the outside, said button holding said pawl (9) in an extreme rearward position of said inner casing locked relative to said outer casing.

4. A feed mechanism defined in one of claims 1 through 3 wherein said inner casing (3) comprises a pawl (15) engaging said rack (4), said rack being forced forward when the inner casing 3 is advanced.

5. A feed mechanism defined in one of claims 1 through 3, wherein said recoil safety means (12) comprises a pawl slanting relative to the longitudinal axis (17) of said feed mechanism (1), entering the path of advance of said rack (4) and affixed to the outer casing (2).

6. A feed mechanism defined in claim 5 wherein said rear end of said inner casing projecting from the outer casing (2) comprises a dosing button (18).

7. An injection device comprising the combination of an ampoule casing for receiving an ampoule of medicine at a forward end thereof so that medicine can be dispensed from a needle attached to a forward end of said ampoule, said ampoule casing having an aperture;

an outer casing (2) attached to said ampoule casing rearwardly of an ampoule received in said ampoule when casing;

an inner casing (3) in said outer casing and protruding rearwardly from said outer casing (2), said inner casing being manually longitudinally movable relative to said outer casing in a forward direction, said inner and outer casings including stop means for limiting said relative movement to a distance (L);

spring means urging said inner casing in a rearward direction;

a toothed rack (4) having a plurality of teeth (5), each tooth having a length (L) corresponding to one full injection dose, said inner casing having means for engaging said rack and moving said rack forward longitudinally of said outer casing against the force of said spring means when said inner casing is moved manually, said rack being adapted to be coupled to an ampoule when said ampoule is received in said ampoule casing to dispense liquid therefrom when said rack is moved forward;

latch means (9, 10) carried by said inner casing for releasably engaging said aperture (11) in said ampoule casing when said inner casing (3) reaches an extreme forward position to thereby prevent motion of said inner casing until said latch means is released; and means (12) for preventing rearward motion of said rack.

* * * * *